(12) United States Patent  (10) Patent No.: US 7,576,203 B2
Shibuya et al.  (45) Date of Patent: Aug. 18, 2009

(54) METHOD FOR PRODUCING CYCLIC DIAMINE DERIVATIVE

(75) Inventors: Kimiyuki Shibuya, Tokorozawa (JP); Ayako Tosaka, Kunitachi (JP)

(73) Assignee: Kowa Co., Ltd., Nagoya-shi (JP)

( * ) Notice: Subject to any disclaimer, the term of this patent is extended or adjusted under 35 U.S.C. 154(b) by 277 days.

(21) Appl. No.: 11/631,397

(22) PCT Filed: Jun. 30, 2005

(86) PCT No.: PCT/JP2005/012041

§ 371 (c)(1), (2), (4) Date: Dec. 29, 2006

(87) PCT Pub. No.: WO2006/003974

PCT Pub. Date: Jan. 12, 2006

(65) Prior Publication Data

US 2008/0045714 A1  Feb. 21, 2008

(30) Foreign Application Priority Data

Jun. 30, 2004  (JP) .............................. 2004-193349

(51) Int. Cl.
*C07D 213/76*  (2006.01)
*C07D 401/12*  (2006.01)
(52) U.S. Cl. ..................... 544/364; 546/296
(58) Field of Classification Search ........................ None
See application file for complete search history.

(56) References Cited

U.S. PATENT DOCUMENTS

| 6,998,486 | B2 | 2/2006 | Shibuya et al. | |
| 7,176,306 | B2 | 2/2007 | Shibuya et al. | |
| 2004/0038987 | A1 * | 2/2004 | Shibuya et al. | 514/253.04 |
| 2006/0035906 | A1 | 2/2006 | Shibuya et al. | |
| 2006/0293519 | A1 | 12/2006 | Shibuya et al. | |

FOREIGN PATENT DOCUMENTS

| WO | WO 91/04027 | 4/1991 |
| WO | 98 54153 | 12/1998 |

OTHER PUBLICATIONS

U.S. Appl. No. 11/631,397, filed Dec. 29, 2006, Shibuya, et al.

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention provides an industrially useful method for synthesizing a cyclic diamine derivative (4) or a salt thereof which serves as an ACAT inhibitor.

A 2-hydroxyacetylaminopyridine compound represented by formula (1), and a method for producing a cyclic diamine derivative represented by formula (4) or a salt thereof from compound (1) through 1) Step A-1, 2) Steps B-1 and B-2, or 3) Steps B-1, B-3, and B-4.

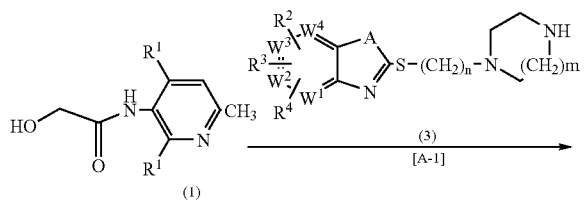

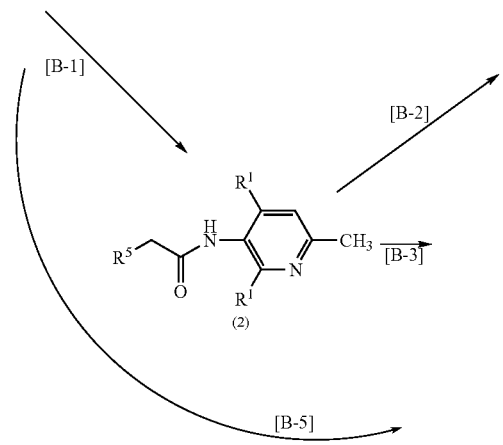

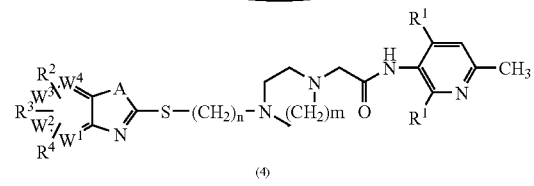

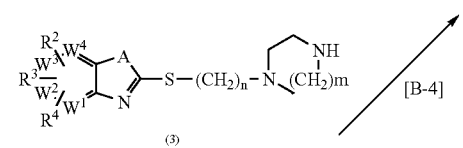

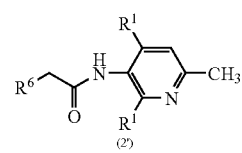

20 Claims, 1 Drawing Sheet

METHOD FOR PRODUCING CYCLIC DIAMINE DERIVATIVE

TECHNICAL FIELD

The present invention relates to an intermediate useful for producing a cyclic diamine derivative and to a method for producing a cyclic diamine compound using the same.

BACKGROUND ART

Acyl-coenzyme A cholesterol acyltransferase (ACAT) is an enzyme which catalyzes synthesis of cholesterol esters from cholesterol and plays an important role in metabolism and absorption of cholesterol through the digestive tract. Recent studies have clarified that when activity of ACAT present in the small intestine and liver is inhibited, elevation of blood cholesterol can be effectively prevented. Thus, extensive research efforts have been made on ACAT inhibitors.

Having focused on a specific type of ACAT that is present in the vascular wall, the applicants previously studied a substance which selectively inhibits the ACAT, and found that, among azole compounds having a cyclic diamine structure, cyclic diamine derivatives represented by the following formula (4'):

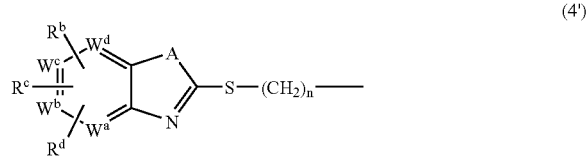

(4')

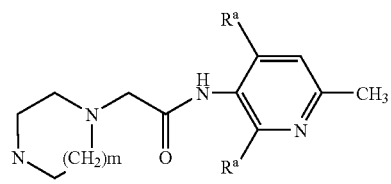

(wherein A is NH, O, or S; each of $W^a$ to $W^d$ is CH, or one of $W^a$ to $W^d$ is N; $R^a$ is lower alkylthio group, lower alkoxy group or halo lower alkoxy group, or lower alkoxy lower alkoxy group; $R^b$, $R^c$, and $R^d$ are each a hydrogen atom, a halogen atom, lower alkyl group, lower alkoxy group, lower alkoxycarbonyl group, halo lower alkyl group, halo lower alkoxy group, lower alkoxy lower alkyl group, lower alkoxy lower alkoxy group, hydroxy lower alkyl group, hydroxy lower alkoxy group, lower alkylcarbonyl group, lower alkylthio group, lower alkylsulfinyl group, lower alkylsulfonyl group, nitro group, or cyano group; m is an integer of 1 or 2; and n is an integer of 1 to 6) and salts thereof are useful therapeutic drugs for hyperlipidemia and arteriosclerosis by virtue of less side effect, excellent water-solubility, and oral absorption. They filed an international patent application on the basis of these findings (Patent Document 1).

The mentioned patent application discloses a method for producing a cyclic diamine derivative (4') through the below-described production method 1 (Example 24) and production method 2 (Example 88). The application also discloses production of a compound (e) via compounds (a) to (c) in accordance with the method described in Patent Document 2. However, the methods disclosed therein have the following problems. That is, since chlorine atoms of a starting compound (a) are highly reactive, when reaction for introducing lower alkylthio groups is carried out in methanol, compounds having methoxy group at the 4- (or 2-) position are produced as byproducts. Moreover, a subsequent reaction for reducing the nitro group of nitropyridine (b) having introduced lower alkylthio groups gives an amine compound (c) accompanied with byproducts without alkylthio group(s). This leads to a further problem of the presence of impurities that are difficult to remove from compound (e).

On the other hands, production method 2 involves the following problems. That is, in reaction steps for producing a target compound (p) starting from compound (m) via intermediate (n) and reaction with (o), compound (n) is unstable, permitting formation of an aziridinium intermediate, which raises an issue of byproducts.

In manufacture of a drug substance, in addition to stable supply, reasonable and efficient control of impurities in each production step is required. The presence of byproducts ultimately leads to the necessity of control of the impurity profile of a pharmaceutical substance.

Production method 1

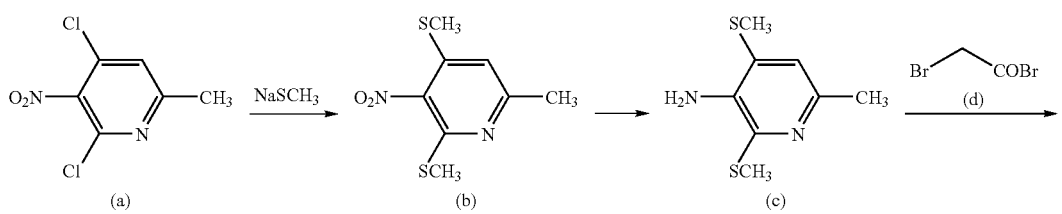

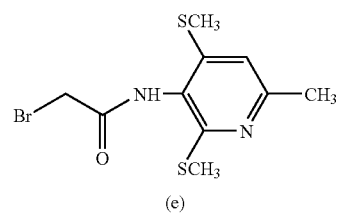

(e)

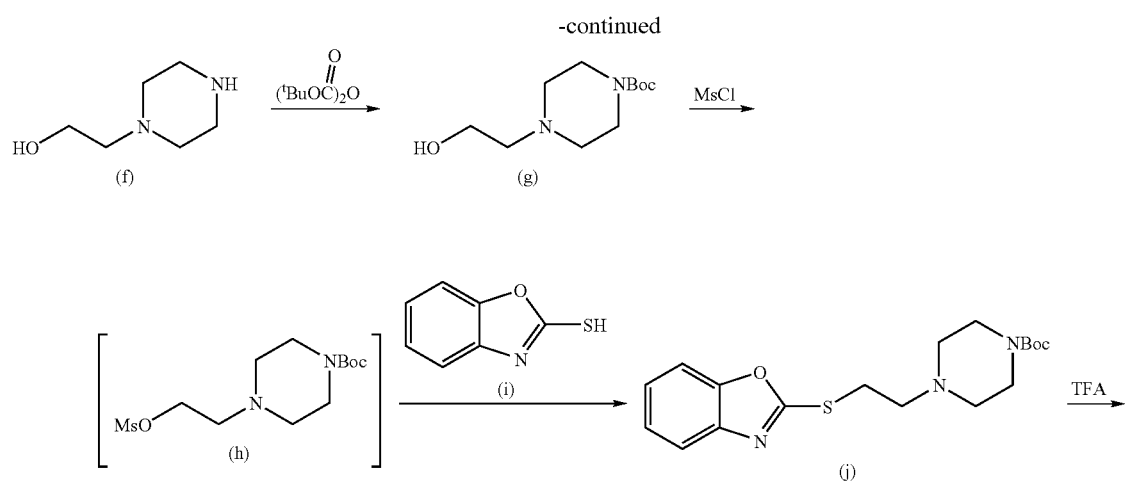
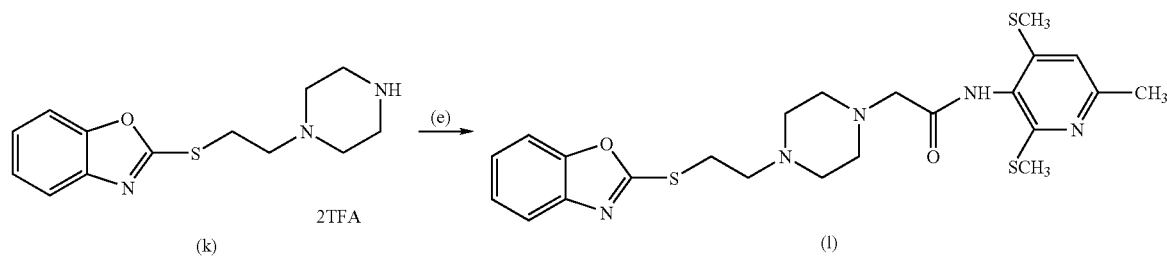
Production method 2
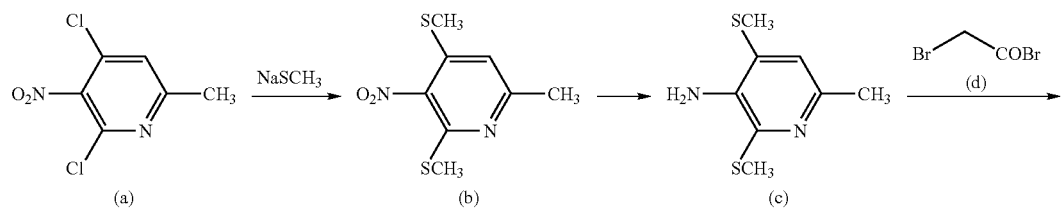
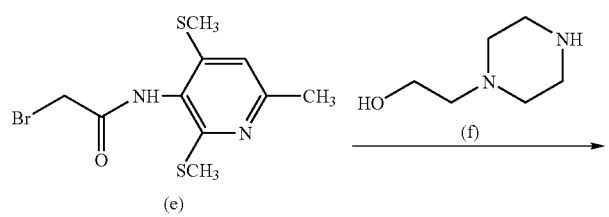
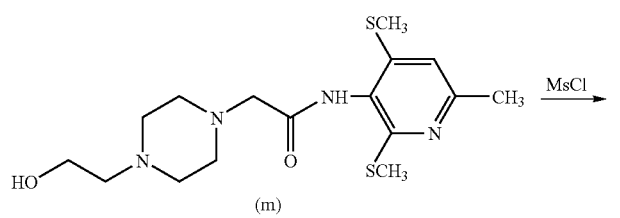

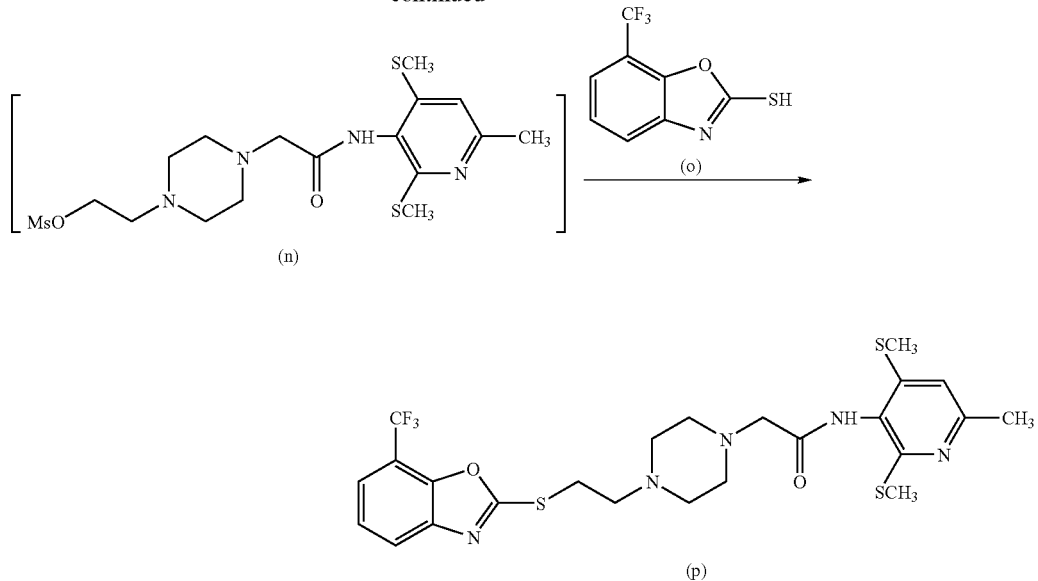

Patent Document 1: Pamphlet of International Publication WO 98/54153

Patent Document 2: Japanese Patent Publication (kokoku) No. 25974/1996

DISCLOSURE OF THE INVENTION

Problems to be Solved by the Invention

An object of the present invention is to provide an industrially useful method for synthesizing a cyclic diamine derivative (4) or a salt thereof which serves as an ACAT inhibitor.

Means for Solving the Problems

Under such circumstances, the present inventors have conducted extensive studies, and have found that a variety of cyclic diamine derivatives (4) or a salt thereof can be produced at high yield and high purity through a method employing a novel 2-hydroxyacetylaminopyridine compound (1) which can be obtained from 3-amino-2,4-dihalogeno-6-methylpyridine (5) serving as a starting material, as shown in the following scheme:

[F3]
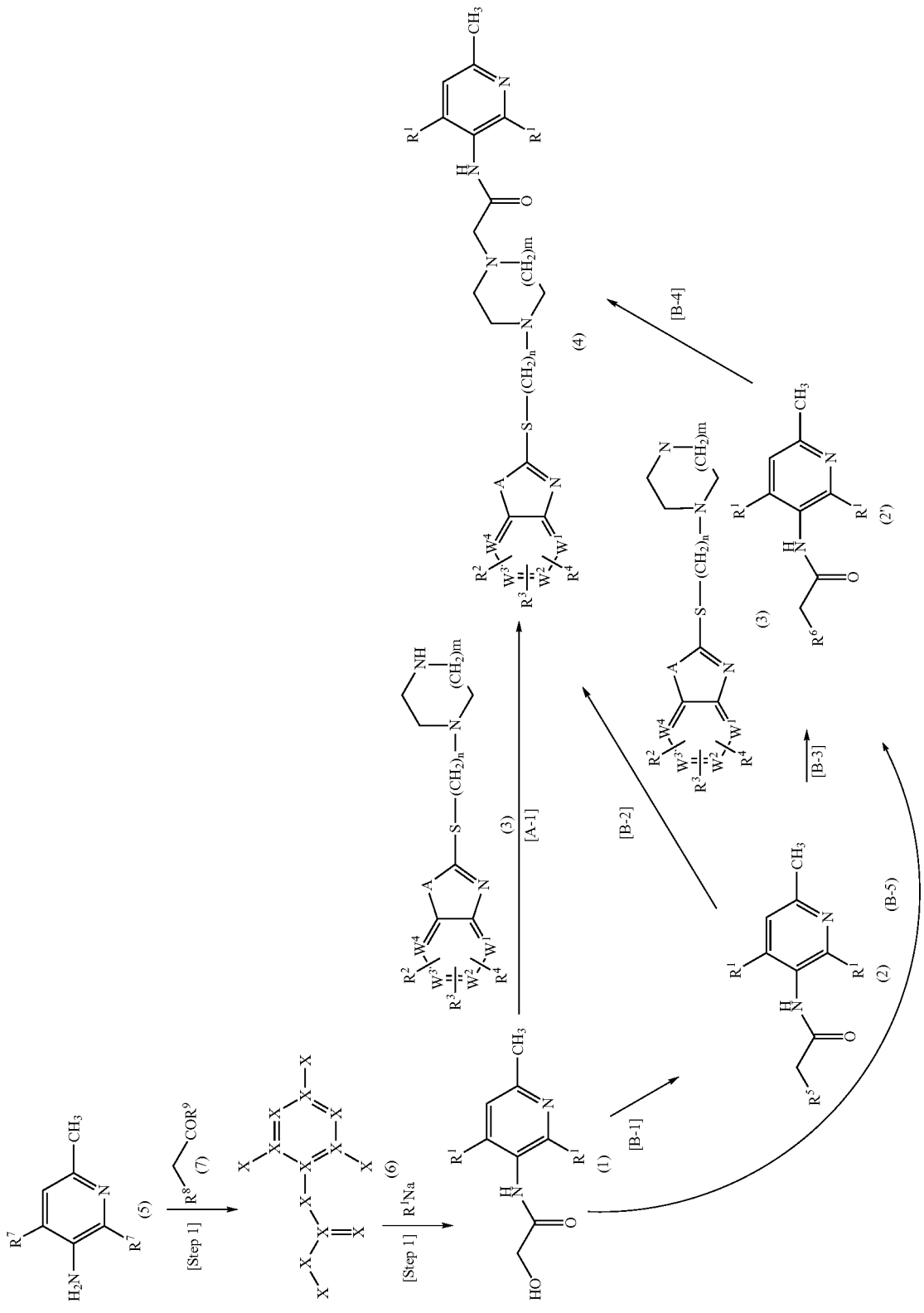

(wherein A is NH, O, or S; each of $W^1$ to $W^4$ is CH, or one of $W^1$ to $W^4$ is N; $R^1$ is lower alkylthio group; $R^2$, $R^3$, and $R^4$ is each a hydrogen atom, a halogen atom, lower alkyl group, lower alkoxy group, lower alkoxycarbonyl group, halo lower alkyl group, halo lower alkoxy group, lower alkoxy lower alkyl group, lower alkoxy lower alkoxy group, hydroxy lower alkyl group, hydroxy lower alkoxy group, lower alkylcarbonyl group, lower alkylthio group, lower alkylsulfinyl group, lower alkylsulfonyl group, nitro group, or cyano group; $R^5$ is sulfonyloxy group; $R^6$ is a halogen atom; $R^7$ (denotes) is a halogen atom; $R^8$ denotes acyloxy group; m is an integer of 1 or 2; n is an integer of 1 to 6). The present invention has been accomplished on the basis of this finding.

Accordingly, the present invention provides a 2-hydroxyacetylaminopyridine compound represented by formula (1).

The present invention also provides a method for producing a cyclic diamine derivative represented by formula (4) or a salt thereof, characterized in that the method comprises reacting a 2-hydroxyacetylaminopyridine compound represented by formula (1) with a piperazine derivative represented by formula (3) or a salt thereof in the presence of a phosphorus compound.

The present invention also provides a method for producing a cyclic diamine derivative represented by formula (4) or a salt thereof, characterized in that the method comprises converting the hydroxy group of a 2-hydroxyacetylaminopyridine compound represented by formula (1) to a sulfonyloxy group to thereby produce a 2-sulfonyloxyacetylaminopyridine compound represented by formula (2); and, subsequently reacting the thus-produced compound with a piperazine derivative represented by formula (3) or a salt thereof; or, subsequently converting the sulfonyloxy group of the sulfonyloxy compound (2) to a halogen atom to thereby produce a 2-haloacetylaminopyridine compound represented by formula (2'), followed by reaction with a piperazine derivative (3).

The present invention also provides a 2-sulfonyloxyacetylaminopyridine compound represented by formula (2).

EFFECTS OF THE INVENTION

The 2-hydroxyacetylaminopyridine compound (1) of the present invention can be efficiently produced from 3-amino-2,4-dihalogeno-6-methylpyridine (5). Moreover, from the thus-prepared compound (1), cyclic diamine derivative (4) or a salt thereof can be produced in a single step, or in 2 to 3 steps. Thus, according to the method of the present invention, since compound (2') does not entrain byproducts which are difficult to remove, the final product; i.e., a cyclic diamine compound (4) or a salt thereof, can be purified easily, facilitating the control of an impurity profile. Moreover, a highly pure cyclic diamine derivative (4) or a salt thereof can be produced in a reduced number of steps (or 1 step) in good yield.

BEST MODE FOR CARRYING OUT THE INVENTION

Figure 1:
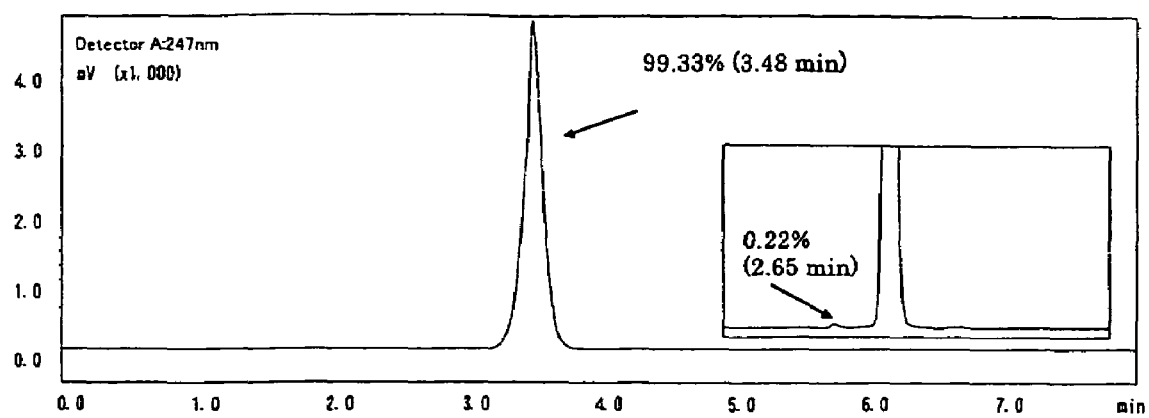
[FIG. 1] Analytical charts showing HPLC purity of N-[2,4-bis(methylthio)-6-methylpyridin-3-yl]-2-bromoacetamide (upper chart: compound produced through an invention method, lower chart: compound produced through a comparative method).
Figure 1:
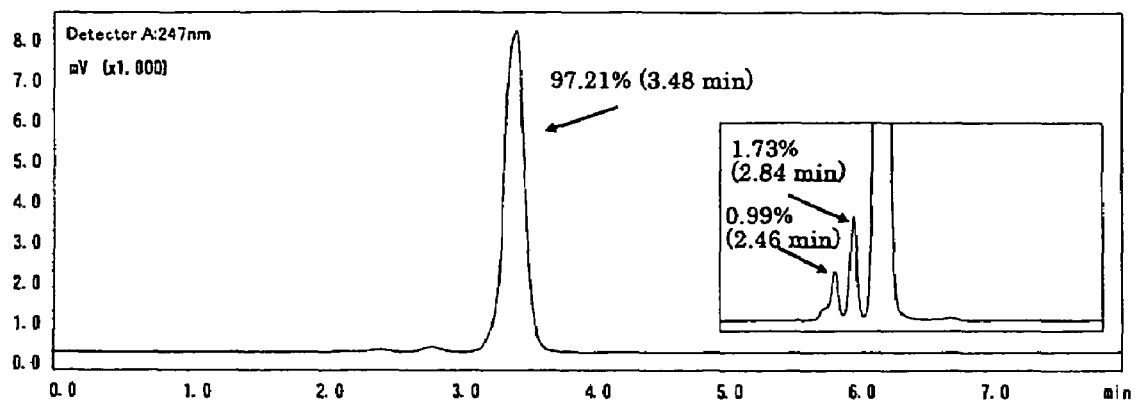

In a substituent represented by $R^1$, $R^2$, $R^3$, or $R^4$ in the chemical formulas provided herein, a lower alkyl group and a lower alkyl moiety of a lower alkoxy group refer to a linear, branched, or cyclic C1-C6 hydrocarbon group.

Examples of the lower alkylthio group represented by $R^1$ include methylthio group, ethylthio group, n-propylthio group, isopropylthio group, cyclopropylthio group, cyclopropylmethylthio group, n-butylthio group, and cyclohexylthio group.

Examples of the lower alkyl group represented by $R^2$, $R^3$, or $R^4$ include methyl group, ethyl group, n-propyl group, tert-butyl group, and isopropyl group. Similarly, examples of the lower alkoxy group include methoxy group, ethoxy group, n-propoxy group, isopropoxy group, n-butoxy group, cyclopropylmethyloxy group, cyclopropyloxy group, cyclohexyloxy group, cyclopentyloxy group, and cyclobutyloxy group. Examples of the lower alkoxycarbonyl group include methoxycarbonyl group, ethoxycarbonyl group, n-propoxycarbonyl group, and tert-butoxycarbonyl group. Examples of the halo lower alkyl group include trifluoromethyl group, and 2,2,2-trifluoroethyl group. Examples of the halo lower alkoxy group include difluoromethoxy group, trifluoromethoxy group, and 2,2,2-trifluoroethoxy group. Examples of the lower alkoxy lower alkyl group include methoxymethyl group, ethoxymethyl group, and methoxyethyl group. Examples of the lower alkoxy lower alkoxy group include methoxymethoxy group, ethoxymethoxy group, methoxyethoxy group, and ethoxyethoxy group. Examples of the hydroxy lower alkyl group include hydroxymethyl group, 2-hydroxyethyl group, 2-hydroxy-2,2-dimethylethyl group, and 3-hydroxy(n-propyl) group. Examples of the hydroxy lower alkoxy group include 2-hydroxyethoxy group, and 3-hydroxy(n-propoxy) group. Examples of the lower alkylcarbonyl group include acetyl, propionyl group, and butyryl group. Examples of the lower alkylthio group include methylthio group, ethylthio group, n-propylthio group, and isopropylthio group. Examples of the lower alkylsulfinyl group include methylsulfinyl group, ethylsulfinyl group, n-propylsulfinyl group, and isopropylsulfinyl group. Examples of the lower alkylsulfonyl group include methylsulfonyl group, ethylsulfonyl group, n-propylsulfonyl group, and isopropylsulfonyl group.

Examples of the halogen atom represented by $R^2$, $R^3$, or $R^4$ include fluorine, chlorine, bromine, and iodine.

Examples of the sulfonyloxy group represented by $R^5$ include alkylsulfonyloxy group and arylsulfonyloxy group. Examples of the alkylsulfonyloxy group include methanesulfonyloxy group, chloromethanesulfonyloxy group, ethanesulfonyloxy group, and propanesulfonyloxy group. Examples of the arylsulfonyloxy group include benzenesulfonyloxy group and p-toluenesulfonyloxy group.

Examples of the halogen atom represented by $R^6$ or $R^7$ include chlorine, bromine, and iodine. Of these, chlorine and bromine are preferred.

Examples of "acyl" of the acyloxy group represented by $R^8$ include acetyl group, propionyl group, and benzoyl group.

m is an integer of 1 or 2, and n is an integer of 1 to 6. Preferably, m is 1 and n is 2 or 3.

According to the present invention, a cyclic diamine derivative (4) or a salt thereof can be produced from compound (1) through a single step (Method A) or 2 to 3 steps (Method B), as described hereinbelow. Notably, compound (1) is a novel compound which has never been reported in the literature.

Method A: Compound (1) is reacted with a piperazine derivative (3) or a salt thereof in the presence of a phosphorus compound (Step A-1).

Method B: The hydroxyl group of compound (1) is converted to a leaving group to thereby produce compound (2)

(Step B-1). Alternatively, compound (2) is further subjected to halogenation to thereby produce compound (2') (Step B-3). The thus-produced compound (2) or (2') is reacted with a piperazine derivative (3) or a salt thereof (Step B-2 or Step B-4).

Each of the above production steps will next be described.

(1) Method A

[Step A-1]

Examples of the phosphorus compound employed in Step A-1 include a phosphine reagent employed in Mitsunobu Reaction; a phosphorus-containing reagent formed of the phosphine reagent with an azo reagent or an ethylenedicarboxylic acid reagent such as dimethyl maleate or N,N,N',N'-tetramethylfumaramide; and a phosphonium ylide reagent.

Examples of preferred modes for carrying out Step A-1 include [1] a method including reacting compound (1) with a piperazine derivative (3) or a salt thereof in the presence of a phosphine reagent and an azo reagent or an ethylenedicarboxylic acid reagent such as dimethyl maleate or N,N,N',N'-tetramethylfumaramide (First Method), [2] a method including reacting compound (1) with a piperazine derivative (3) or a salt thereof in the presence of a phosphonium ylide reagent (Second Method).

In First Method, compound (1), a piperazine derivative (3) or a salt thereof, and a phosphine reagent are dissolved in a reaction solvent, and an azo reagent or an ethylenedicarboxylic acid reagent is added to the solution. The mixture is allowed to react under argon or nitrogen, at 0° C. to 100° C., preferably at room temperature to 80° C., for 2 hours to 1 day.

Examples of the phosphine reagents which are employed in the reaction include trialkylphosphines such as trimethylphosphine, triethylphosphine, tripropylphosphine, triisopropylphosphine, tributylphosphine, triisobutylphosphine, and tricyclohexylphosphine and triarylphosphines such as triphenylphosphine and diphenylphosphinopolystyrene. Of these, trimethylphosphine, tributylphosphine, and triphenylphosphine are preferred.

Examples of the azo reagent include diethyl azodicarboxylate (DEAD), diisopropyl azodicarboxylate, 1,1'-azobis(N,N-dimethylformamide) (TMAD), 1,1'-(azodicarbonyl)dipiperidine (ADDP), 1,1'-azobis(N,N-diisopropylformamide) (TIPA), and 1,6-dimethyl-1,5,7-hexahydro-1,4,6,7-tetrazocine-2,5-dione (DHTD). Of these, diethyl azodicarboxylate is preferred.

Examples of the reaction solvent employed in the reaction include N,N-dimethylformamide (DMF), tetrahydrofuran, dioxane, acetonitrile, nitromethane, acetone, ethyl acetate, benzene, chlorobenzene, toluene, chloroform, and methylene chloride. Of these, DMF, tetrahydrofuran, dioxane, and acetonitrile are preferred, with DMF and tetrahydrofuran being more preferred.

In Second Method, compound (1), a piperazine derivative (3) or a salt thereof, and a phosphonium ylide reagent are dissolved in a reaction solvent. The mixture is allowed to react under argon or nitrogen, at room temperature to 120° C., preferably at 80° C. to 100° C., for 2 hours to 12 hours.

Examples of the phosphonium ylide reagent which is employed in the reaction include alkanoylmethylenetrialkylphosphorane, alkanoylmethylenetriarylphosphorane, alkoxycarbonylmethylenetrialkylphosphorane, alkoxycarbonylmethylenetriarylphosphorane, cyanomethylenetrialkylphosphorane, and cyanomethylenetriarylphosphorane. Examples of the trialkyl include trimethyl, triethyl, tripropyl, triisopropyl, tributyl, triisobutyl, and tricyclohexyl, and examples of the triaryl include triphenyl and diphenylpolystyrene.

Alternatively, in the above reaction, a phosphonium ylide reagent may be generated in the reaction system through reacting a phosphonium halide reagent with compound (1) and a piperazine derivative (3) or a salt thereof in the presence of a base.

Examples of the phosphonium halide reagent employable in the alternative method include (cyanomethyl)trialkylphosphonium halide, (cyanomethyl)triarylphosphonium halide, (alkylcarbonylmethyl)trialkylphosphonium halide, (alkylcarbonylmethyl)triarylphosphonium halide, (alkoxycarbonylmethyl)trialkylphosphonium halide, and (alkoxycarbonylmethyl)triarylphosphonium halide.

Notably, among the aforementioned phosphonium halide reagents, (cyanomethyl)trialkylphosphonium halide and (cyanomethyl)triarylphosphonium halide can be prepared through reacting the corresponding trialkylphosphine or triarylphosphine with the corresponding haloacetonitrile (Tetrahedron, vol. 57, pp. 5451-5454, 2001). Similarly, each of the other phosphonium halide reagents can be prepared through reacting the corresponding trialkylphosphine or triarylphosphine with the corresponding alkanoylhalomethyl or alkoxycarbonylhalomethyl. Examples of trialkylphosphine and triarylphosphine employed herein include the same compounds as shown in Method A. Of these, trimethylphosphine, tributylphosphine, and triphenylphosphine are preferred, with trimethylphosphine being particularly preferred.

Examples of the aforementioned alkanoyl include formyl, acetyl, propionyl, and butyryl. Of these, acetyl and propionyl are preferred. Examples of the alkoxy in the alkoxycarbonyl include methoxy, ethoxy, propoxy, and butoxy. Of these, methoxy, ethoxy, and butoxy are preferred.

As the halogen atom, chlorine, bromine, and iodine are preferred.

Examples of the base include organic bases such as triethylamine, N,N-diisopropylethylamine, 1,4-diazabicyclo[2,2,2]octane (DABCO), 1,8-diazabicyclo[5,4,0]undec-7-ene (DBU), and 1,5-diazabicyclo[4,3,0]non-5-ene (DBN); and inorganic bases such as potassium carbonate, sodium carbonate, cesium carbonate, lithium carbonate, lithium diisopropylamide, and potassium hexamethyldisilazide. Of these, N,N-diisopropylethylamine, potassium carbonate, lithium diisopropylamide, and potassium hexamethyldisilazide are preferred, with N,N-diisopropylethylamine and potassium carbonate being particularly preferred.

Examples of preferred reaction solvents include dioxane, tetrahydrofuran, toluene, benzene, DMF, dimethyl sulfoxide, acetonitrile, and propionitrile. Of these, propionitrile is particularly preferred.

A piperazine derivative (3) or a salt thereof can be produced through a method described in Pamphlets of International Publication WO 98/54153 (mentioned hereinbefore) and WO 03/057675, or an analogous method.

In the above reaction (Method A), a piperazine derivative (3) or a salt thereof may be employed. In order to enhance the yield, use of a salt of the piperazine derivative (3) is preferred. Examples of the salt include hydrochlorides, hydrobromides, hydroiodides, methanesulfonates, trifluoroacetates, benzenesulfonates, and p-toluenesulfonates, with hydroiodides being particularly preferred.

(2) Method B

[Step B-1]

Compound (2) can be obtained through converting the hydroxyl group of compound (1) to a sulfonyloxy group. The thus-obtained compound (2) is also a novel compound which has never been reported in the literature.

The above reaction may be performed by use of a reagent such as a sulfonate-esterfying agent. For example, compound (1) is dissolved in a solvent, and a sulfonate-esterfying agent is added to the solution. Sulfonate-esterification is performed, in the presence or absence of a base, preferably at 0 to 60° C., more preferably 0° C. to room temperature, for 0.5 to 10 hours.

Examples of preferred sulfonate-esterfying agents include methanesulfonyl chloride, methanesulfonic anhydride, benzenesulfonyl chloride, p-toluenesulfonyl chloride.

Examples of the base include organic bases such as triethylamine, 4-dimethylaminopyridine, N,N-diisopropylethylamine, and pyridine; alkali metal carbonates such as potassium carbonate and sodium carbonate; and alkali metal hydrogencarbonates such as potassium hydrogencarbonate and sodium hydrogencarbonate.

Examples of the solvent which may be employed include tetrahydrofuran, acetonitrile, DMF, ethyl acetate, methylene chloride, chloroform, toluene, and dimethyl sulfoxide.

[Step B-3]

Compound (2') can be obtained through converting the sulfonyloxyl group of compound (2) to a halogen atom.

In a preferred mode, compound (2) is dissolved in a solvent, and reacted with a halide salt at 0 to 60° C., more preferably 0° C. to room temperature, for 0.5 to 10 hours. Examples of the halide salt include metal halide salts such as lithium iodide, lithium bromide, lithium chloride, sodium iodide, sodium bromide, and sodium chloride; and quaternary tetraalkylammonium salts such as tetramethylammonium iodide, tetramethylammonium bromide, tetramethylammonium chloride, tetraethylammonium iodide, tetraethylammonium bromide, tetraethylammonium chloride, tetrabutylammonium iodide, tetrabutylammonium bromide, tetrabutylammonium chloride, benzyltrimethylammonium iodide, benzyltrimethylammonium bromide, and benzyltrimethylammonium chloride. Of these, lithium bromide and sodium bromide are preferred, with sodium bromide being more preferred.

Alternatively, compound (2') can be obtained through converting the hydroxyl group of compound (1) to a halogen atom (B-5).

Specifically, compound (1) may be dissolved in a solvent, and reacted with a halogenating agent in the presence or absence of a base, to thereby obtain compound (2'). The above reaction may be performed at 0 to 100° C., preferably 0° C. to 60° C., for 0.5 to 10 hours.

Examples of the halogenating agent include chlorinating agents and brominating agents such as phosphorus oxychloride, phosphorus pentachloride, triphenylphosphine dichloride, triphenylphosphine dibromide, triphenylphosphite dichloride, triphenylphosphite dibromide, phosphorus tribromide, thionyl chloride, triphenylphosphine and tetrachloromethane, triphenylphosphine and tetrabromomethane, triphenylphosphine and N-bromosuccinimide, and methanesulfonyl chloride and 4-dimethylaminopyridine, with triphenylphosphine and N-bromosuccinimide being preferred.

Examples of the solvent which may be employed include dichloromethane, chloroform, benzene, toluene, tetrahydrofuran, pyridine, and DMF.

The compound (2') produced through the above method is significantly superior to compound (e) prepared through production method 1 or 2 described hereinbefore, in terms of impurities (see Comparative Examples). Thus, method B of the present invention (step B-1, step B-3, step B-4) facilitates the control of the impurity profile as compared with conventional methods and enables efficient production of a highly pure target substance.

[Step B-2] and [Step B-4]

The cyclic diamine derivative or a salt thereof can be produced through reacting compound (2) or compound (2') with a piperazine derivative (3) or a salt thereof in the presence or absence of a base.

The reaction of alkylating the amino group is performed through adding a piperazine derivative (3) or a salt thereof to a solution of compound (2) or compound (2') in the presence or absence of a base.

Examples of the base include inorganic bases such as alkali metal carbonates (e.g., potassium carbonate and sodium carbonate) and alkali metal hydrogencarbonates (e.g., potassium hydrogencarbonate and sodium hydrogencarbonate); and organic bases such as pyridine, triethylamine, N,N-diisopropylethylamine, 1,8-diazabicyclo[5.4.0]-7-undecene (DBU), 1,4-diazabicyclo-[2.2.2]octane (DABCO), and N,N-dimethylaniline, with potassium carbonate being more preferred.

Examples of the solvent which may be employed include acetonitrile, acetone, tetrahydrofuran, and DMF. If necessary, an aqueous solvent system thereof may be employed. Preferably, acetonitrile is employed.

Preferably, the reaction is performed at 0 to 80° C., more preferably at room temperature, for 0.5 hours to 1 day.

A 2-hydroxyacetylaminopyridine (1) can be produced through, for example, Step-1 and Step-2.

[Step-1]

An acetamide compound (6) is obtained through acylating 3-amino-2,4-dihalogeno-6-methylpyridine (5) in a solution in the presence of a base by use of an acid halide derivative (7).

Examples of the base include organic bases such as pyridine, triethylamine, N,N-diisopropylethylamine, 4-dimethylaminopyridine, N,N-dimethylaniline, and N,N-diethylaniline; and inorganic bases such as alkali metal hydrogencarbonates (e.g., potassium hydrogencarbonate and sodium hydrogencarbonate) and alkali metal carbonates (e.g., potassium carbonate and sodium carbonate), with N,N-dimethylaniline being particularly preferred.

Examples of preferred solvents which may be employed include methylene chloride, chloroform, 1,2-dichloroethane, acetonitrile, tetrahydrofuran, ethyl acetate, benzene, and toluene. Preferably, the reaction is performed at 0 to 80° C., more preferably 0° C. to room temperature, for 0.5 hours to 1 day.

[Step-2]

Compound (1) can be obtained through converting a halogen atom of 2-acyloxyacetylaminopyridine compound (6) to a lower alkylthio group and removing the acyl group.

Specifically, the reaction may be performed through adding sodium lower alkylthio alkoxide powder, a solution of the powder in an organic solvent, or an aqueous solution of the powder to a solution of compound (6) and 18-crown-6.

Preferably, sodium lower alkylthioalkoxide is employed in an amount of 2.5 to 20 eqs. with respect to compound (6), and 18-crown-6 is employed in an amount of 0.05 to 0.5 eqs. with respect to compound (6).

Examples of the solvent include isopropyl alcohol, dimethyl sulfoxide, DMF, N-methylpyrrolidone, and toluene. Of these, dimethyl sulfoxide is particularly preferred.

Preferably, the reaction is performed at room temperature to 150° C., more preferably at 70 to 85° C., for 1 hour to 1 day.

EXAMPLES

The present invention will next be described in more detail by way of examples.

Production Example 1

Synthesis of N-[2,4-dichloro-6-methylpyridin-3-yl]-2-acetyloxyacetamide

N,N-Dimethylaniline (142.4 g, 1,175 mmol) was added to a solution of 3-amino-2,4-dichloro-6-methylpyridine (130.0 g, 734 mmol) in chloroform (910 mL). Under cooling with water, a solution of acetyloxyacetyl chloride (150.4 g, 1,102 mmol) in chloroform (390 mL) was added dropwise thereto over 30 minutes while the temperature of the reaction mixture was maintained at 19 to 27° C., followed by stirring at room temperature overnight (18 hours). After HPLC was performed to confirm that starting materials had been completely consumed, water (650 mL) was added to the reaction mixture. The formed organic layer was collected, and the aqueous layer was extracted with chloroform (650 mL). The obtained organic layers were combined, followed by washing sequentially with water and saturated brine. The thus-washed organic layer was dried over sodium sulfate anhydrate, and the solvent was removed under reduced pressure. Subsequently, isopropyl alcohol (195 mL) and diisopropyl ether (390 mL) were added to the residue, and the resultant mixture was heated for dissolution. Diisopropyl ether (650 mL) was added dropwise thereto at an internal temperature of 62 to 66° C. The reaction mixture was cooled, followed by stirring for 3.5 hours under cooling with ice. The crystals that precipitated were collected through filtration, followed by washing with a cooled mixture of isopropyl alcohol (19.5 mL) and diisopropyl ether (104 mL). The obtained mixture was dried at room temperature under reduced pressure, to thereby yield N-[2,4-dichloro-6-methylpyrrolidin-3-yl]-2-acetyloxyacetamide as colorless crystals (171.7 g, 619.6 mmol, yield: 84.4%, HPLC: 99.20%).

Melting point: 119-120° C.

IR(neat)cm$^{-1}$: 3238, 1749, 1691, 1582, 1555.

$^1$H-NMR (CDCl$_3$) δ: 2.25 (3H, s), 2.54 (3H, s), 4.79 (2H, s), 7.25 (1H, s), 7.60 (1H, s).

Elemental analysis: as C$_{10}$H$_{10}$Cl$_2$N$_2$O$_3$

Calculated: C, 43.34; H, 3.64; N, 10.11.

Found: C, 43.33; H, 3.53; N, 10.07.

Example 1

Synthesis of N-[2,4-bis(methylthio)-6-methylpyridin-3-yl]-2-hydroxyacetamide (A) Sodium thiomethoxide powder (5.06 g, 72.19 mmol) was added to a solution of N-[2,4-dichloro-6-methylpyridin-3-yl]-2-acetyloxyacetamide (5.00 g, 18.04 mmol) and 18-crown-6 (0.48 g, 1.82 mmol) in dimethyl sulfoxide (40 mL), followed by stirring at an internal temperature of 75 to 81° C. for 1 hour. After the reaction mixture was left to cool, chloroform and water were added thereto. The formed organic layer was separated, and the aqueous layer was extracted with chloroform. The obtained organic layers were combined, followed by washing sequentially with water and saturated brine. The thus-washed organic layer was dried over sodium sulfate anhydrate, and the solvent was removed under reduced pressure. The aqueous layer obtained in the above washing was extracted with chloroform, and the organic layer was washed sequentially with water and saturated brine. The thus-washed organic layer was dried over sodium sulfate anhydrate, and the solvent was removed. The residues were combined, followed by purification through silica gel column chromatography (hexane/acetone=5/2), to thereby yield N-[2,4-bis(methylthio)-6-methylpyridin-3-yl]-2-hydroxyacetamide as a colorless solid (4.06 g, yield: 87.1%). The solid was recrystallized from ethyl acetate, to thereby yield colorless needles.

(B) N-[2,4-Dichloro-6-methylpyridin-3-yl]-2-acetyloxyacetamide (135.0 g, 487 mmol) and 18-crown-6 (12.9 g, 48.8 mmol) were dissolved in dimethyl sulfoxide (1,350 mL). Under cooling with water, sodium thiomethoxide (powder) (170.7 g, 2,435 mmol) was added thereto. The reaction mixture was heated, followed by stirring at an internal temperature of 50 to 55° C. for 2.5 hours. After the reaction mixture was water-cooled, water (1,350 mL) and chloroform (1,350 mL) were added thereto. The formed organic layer was collected, and the aqueous layer was extracted with chloroform (675 mL). The obtained organic layers were combined, followed by washing with saturated brine (2,025 mL). The thus-washed organic layer was dried over sodium sulfate anhydrate, and the solvent was removed under reduced pressure. Subsequently, methanol (135 mL) and water (1,350 mL) were added to the residue, and the resultant mixture was stirred at an internal temperature of 23 to 25° C. for 1.5 hours. The crystals that precipitated were collected through filtration, followed by washing with water and drying at room temperature, to thereby the crude target product. The crude product was dissolved in chloroform (380 mL) through heating, and the reaction mixture was cooled. The cooled mixture was stirred at an internal temperature of 5° C. or lower for 2 hours. The crystals that precipitated were collected through filtration, followed by washing with cooled chloroform (76 mL) and drying at room temperature, to thereby yield N-[2,4-bis(methylthio)-6-methylpyridin-3-yl]-2-hydroxyacetamide (68.49 g, yield: 54.4%, HPLC: 97.47%).

Melting point: 166-167° C.

IR(neat): 3268, 1665, 1637, 1583, 1565.

$^1$H-NMR (CDCl$_3$) δ: 2.42 (3H, s), 2.50 (3H, s), 2.52 (3H, s), 2.72 (1H, s), 4.33 (1H, s), 4.35 (1H, s), 6.67 (1H, s), 7.62 (1H, s).

EIMS m/z (relative intensity): 258 (M$^+$), 167 (100)

Elemental analysis: as C$_{10}$H$_{14}$N$_2$O$_2$S$_2$

Calculated: C, 46.49; H, 5.46; N, 10.84.

Found: C, 46.49; H, 5.40; N, 10.81.

Example 2

Synthesis of 2-[4-[2-(benzimidazol-2-ylthio)ethyl]piperazin-1-yl]-N-[2,4-bis(methylthio)-6-methylpyridin-3-yl]acetamide Diethyl azodicarboxylate (1.88 mL, 4.33 mmol) was added dropwise to a solution of N-[2,4-bis(methylthio)-6-methylpyridin-3-yl]-2-hydroxyacetamide (373 mg, 1.44 mmol), 1-[2-(benzimidazol-2-ylthio)ethyl]piperazine (1.40 g, 5.34 mmol), and triphenylphosphine (1.34 g, 5.09 mmol) in dimethylformamide (DMF) (20 mL) under stirring with water cooling over 5 minutes. The resultant mixture was stirred at room temperature for 60 minutes, and water (2 mL) was added thereto so as to deactivate the reagent. The reaction mixture was partitioned between 1N hydrochloric acid (30 mL) and ethyl acetate (30 mL). The formed organic layer was extracted with 1N hydrochloric acid (15 mL×2). The formed aqueous layers were combined, and the thus-combined aqueous layer was washed with ethyl acetate (20 mL×2). The pH of the resultant mixture was adjusted to 8 to 9 with 1N sodium hydroxide. The formed aqueous layer was extracted with ethyl acetate (20 mL×3). The organic layer was washed with saturated brine, and dried over sodium sulfate anhydrate, followed by solvent removal under reduced pressure. The residue was purified through silica gel column chromatography (developer: chloroform:methanol=100:3). The obtained oily substances were crystallyzed from ethanol and ether, to thereby yield 2-[4-[2-(benzimidazol-2-ylthio)ethyl]piperazin-1-yl]-N-[2,4-bis(methylthio)-6-methylpyridin-3-yl]acetamide as colorless crystals (372 mg, yield: 51%).

Example 3

Synthesis of 2-[4-[2-(benzimidazol-2-ylthio)ethyl]piperazin-1-yl]-N-[2,4-bis(methylthio)-6-methylpyridin-3-yl]acetamide p-Toluenesulfonic acid (357 mg, 1.88 mmol) was added to a solution of 1-[2-(benzimidazol-2-ylthio)ethyl]piperazine (493 mg, 1.88 mmol) in tetrahydrofuran (15 mL) under stirring at room temperature. After 5 minutes, the solvent was removed under reduced pressure, to thereby yield 1-[2-(benzimidazol-2-ylthio)ethyl]piperazine toluenesulfonate.

Amberlyst A-26 (50 g) was charged into a column tube, followed by washing sequentially with a 1 mol/L aqueous sodium hydroxide solution (50 mL) and distilled water (300 mL). Subsequently, a 1 mol/L aqueous sodium iodide solution (100 mL) passed therethrough, and the column tube was washed sequentially with methanol (200 mL) and acetone (300 mL), and dried.

The same resin (2.5 g) was charged into the column tube again, and a solution of 1-[2-(benzimidazol-2-ylthio)ethyl]piperazine toluenesulfonate (817 mg, 1.88 mmol) in methanol (30 mL) passed therethrough, followed by washing with methanol (100 mL). The obtained fraction was subjected to removal under reduced pressure, to thereby yield 1-[2-(benzimidazol-2-ylthio)ethyl]piperazine iodate.

Diisopropyl azodicarboxylate (0.770 mL, 1.52 mmol) was added dropwise to a solution of N-[2,4-bis(methylthio)-6-methylpyridin-3-yl]-2-hydroxyacetamide (131 mg, 0.508 mmol), 1-[2-(benzimidazol-2-ylthio)ethyl]piperazine iodate (933 mg, 1.88 mmol) and triphenylphosphine (470 mg, 1.79 mmol) in dimethylformamide (3 mL) under stirring with water cooling over 5 minutes. The resultant mixture was stirred at room temperature for 60 minutes, and water (10 mL) was added thereto. Subsequently, 1 mol/L hydrochloric acid (10 mL) and ethyl acetate (30 mL) were added the reaction mixture, to thereby collect the aqueous layer. The organic layer was extracted with 1 mol/L hydrochloric acid (10 mL×2). The obtained aqueous layers were combined, and the thus-combined aqueous layer was washed with ethyl acetate (30 mL×2). The pH of the resultant mixture was adjusted to 8 to 9 with a 1 mol/L aqueous sodium hydroxide solution, followed by extraction with ethyl acetate (30 mL×3). The organic layers were combined, and the thus-combined organic layer was washed with saturated brine. The thus-washed organic layer was dried over sodium sulfate anhydrate, and the solvent was removed under reduced pressure. The crude product was purified through silica gel column chromatography (silica gel: 40 g, developer: chloroform:methanol=100:3), to thereby yield 2-[4-[2-(benzimidazol-2-ylthio)ethyl]piperazin-1-yl]-N-[2,4-bis(methylthio)-6-methylpyridin-3-yl]acetamide (240 mg, yield: 94%).

Example 4

Synthesis of N-[2,4-bis(methylthio)-6-methylpyridin-3-yl]-2-bromoacetamide

Under cooling with ice, methanesulfonyl chloride (31.7 g, 276.7 mmol) was added dropwise to a solution of N-[2,4-bis(methylthio)-6-methylpyridin-3-yl]-2-hydroxyacetamide (65.0 g, 251.6 mmol), triethylamine (30.5 g, 301.4 mmol), and 4-dimethylaminopyridine (3.07 g, 25.13 mmol) in DMF (455 mL) while the reaction mixture was maintained at 11° C. or lower, followed by stirring for 0.5 hours under cooling with ice. After HPLC was performed to confirm that starting materials had been completely consumed, the crystals (triethylamine hydrochloride) that precipitated were collected through filtration, followed by washing with DMF (195 mL). The filtrate and the wash liquid were combined, and sodium bromide (51.8 g, 503.5 mmol) was added to the resultant mixture. The reaction mixture was stirred under heat at an internal temperature of 55 to 60° C. for 3 hours. Subsequently, water (650 mL) was added to the reaction mixture, and the resultant mixture was stirred at an internal temperature of 21 to 25° C. for 2 hours. The crystals that precipitated were collected through filtration, followed by washing with water and drying through air blow. The crude target product was dissolved in methanol (500 mL) through heating, and the reaction mixture was cooled. The crystals that precipitated were collected through filtration, followed by drying through air blow at 60° C., to thereby yield N-[2,4-bis(methylthio)-6-methylpyridin-3-yl]-2-bromoacetamide (54.38 g, yield: 67.3%, HPLC: 99.32%).

Example 5

Synthesis of 2-[4-[2-(benzimidazol-2-ylthio)ethyl]piperazin-1-yl]-N-[2,4-bis(methylthio)-6-methylpyridin-3-yl]acetamide Acetonitrile (450 mL) and potassium carbonate (85.7 g, 0.62 mol) were added to 1-[2-(benzimidazol-2-ylthio)ethyl]piperazine.3 hydrochloride (59.42 g, 0.16 mol) in water (180 mL). Subsequently, 2-bromo-N-[2,4-bis(methylthio)-6-methylpyridin-3-yl]acetamide (48.19 g, 0.15 mol) was gradually added thereto, and the resultant mixture was stirred at room temperature for 2 hours. The reaction mixture was diluted with water (300 mL), followed by stirring for 1 hour. The crystals that precipitated were separated through filtration, followed by washing with a solvent mixture (600 mL) of acetonitrile and water (1:1), washing with water (200 mL), and drying through air blow at 40 to 50° C., to thereby yield 2-[4-[2-(benzimidazol-2-ylthio)ethyl]piperazin-1-yl]-N-[2,4-bis(methylthio)-6-methylpyridin-3-yl]acetamide as colorless crystals (75 g, yield: 99%).

Example 6

Synthesis of 2-[4-[2-(benzimidazol-2-ylthio)ethyl]piperazin-1-yl]-N-[2,4-bis(methylthio)-6-methylpyridin-3-yl]acetamide In a manner similar to that employed in Example 4, methansulfonyl chloride (62 mg, 0.542 mmol) was added dropwise to a solution of N-[2,4-bis(methylthio)-6-methylpyridin-3-yl]-2-hydroxyacetamide (100 mg, 0.387 mmol), 4-dimethylaminopyridine (4.7 mg, 0.039 mmol), and triethylamine (47 mg, 0.465 mmol) in DMF (1 mL) under cooling with ice under stirring. The resultant mixture was stirred under cooling with ice for 0.5 hours. After TLC was performed to confirm that starting materials had been completely consumed, the crystals (triethylamine hydrochloride) that precipitated were separated through filtration, followed by washing with DMF (1 mL). The filtrate and the wash liquid were combined, and 1-[2-(benzimidaimidazol-2-ylthio) ethyl]piperazine (143 mg, 0.426 mmol) and potassium carbonate (262 mg, 1.49 mmol) were added thereto, the resultant mixture was stirred at room temperature overnight. After completion of reaction, the reaction mixture was extracted with ethyl acetate. The organic layer was washed with saturated brine. The thus-washed organic layer was dried over sodium sulfate anhydrate, and the solvent was removed under reduced pressure. The residue was treated and purified in a manner similar to that employed in Example 4, to thereby yield 2-[4-[2-(benzimidazol-2-ylthio)ethyl]piperazin-1-yl]-N-[2,4-bis(methylthio)-6-methylpyridin-3-yl]acetamide as colorless crystals (117 mg, yield: 61%).

Comparative Example

Synthesis of N-[2,4-bis(methylthio)-6-methylpyridin-3-yl]-2-bromoacetamide

With reference to Example 238 described in Japanese Patent Publication (kokoku) No. 25974/1996, 2,4-bis(methylthio)-3-nitro-6-methylpyridine was obtained, and the thus-obtained nitro compound was dissolved in a mixture of methanol and dioxane, followed by reduction in the presence of Raney nickel in a hydrogen atmosphere. Subsequently, N,N-dimethylaniline (0.85 g, 7 mmol) was added to a suspension of the obtained crude 3-amino-2,4-bis(methylthio)-6-methylpyridine (1.0 g, 5 mmol) in chloroform (15 mL). Under cooling with ice, a solution of bromoacetyl chloride (1.21 g, 6 mmol) in chloroform (3 mL) was added dropwise thereto, and the resultant mixture was stirred at room temperature for 2 hours. Subsequently, TLC was performed to confirm that starting materials had been completely consumed. Thereafter, water (65 mL) was added to the reaction mixture, and the resultant mixture was stirred overnight. The crystals that precipitated were collected through filtration, followed by recrystallization from ethanol and drying through air blow, to thereby yield primary crystals of N-[2,4-bis(methylthio)-6-methylpyridin-3-yl]-2-bromoacetamide (818 mg, yield: 50.9%, HPLC: 97.2%).

FIG. 1 includes charts for comparing a compound obtained from Example 4 with a compound obtained from the Comparative Example in terms of purity as measured through high performance liquid chromatography (HPLC). Measurement apparatus and conditions employed in high performance liquid chromatography are as follows.

Apparatus: Shimadzu high performance liquid chromatography LC-2010A HT
Column: CAPCELL PAK UG120 5 mm 4.6 mm×150 mm
Mobile phase: 5 mMSLS/10 mM $H_3PO_4$:$CH_3CN$=50:50
Flow rate: 1 mL/min
Detection wavelength: 247 nm
Column temperature: 40° C.

FIG. 1 reveals that, as compared with a compound produced through a comparative method, a compound prepared according to the present invention has significantly suppressed amounts of impurities, showing that the invention compounds are useful for a large-scale and stable supply of pharmaceutical substances.

The invention claimed is:
1. A 2-hydroxyacetylaminopyridine compound represented by formula (1):

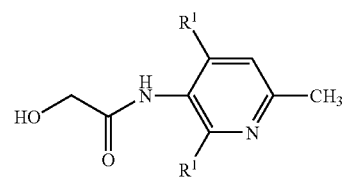

wherein $R^1$ is a lower alkylthio group.

2. A method for producing a cyclic diamine represented by formula (4) or a salt thereof:

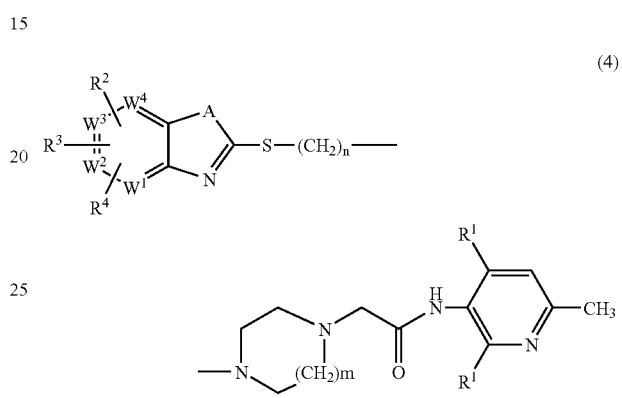

wherein A is NH, O, or S; each of $W^1$ to $W^4$ is CH, or one of $W^1$ to $W^4$ is N; $R^1$ is a lower alkylthio group; $R^2$, $R^3$, and $R^4$ may be identical to or different from one another, and each is a hydrogen atom, a halogen atom, lower alkyl group, lower alkoxy group, lower alkoxycarbonyl group, halo lower alkyl group, halo lower alkoxy group, lower alkoxy lower alkyl group, lower alkoxy lower alkoxy group, hydroxy lower alkyl group, hydroxy lower alkoxy group, lower alkylcarbonyl group, lower alkylthio group, lower alkylsulfinyl group, lower alkylsulfonyl group, nitro group, or cyano group or a salt thereof, the method comprising reacting a 2-hydroxyacetylaminopyridine compound represented by formula (1):

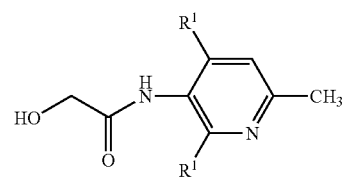

wherein $R^1$ has the same meaning as described above with a piperazine represented by formula (3):

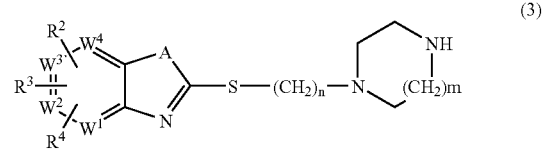

wherein A, $W^1$ to $W^4$, $R^2$ to $R^4$, m and n have the same meanings as described above or a salt thereof in the presence of a phosphorus compound.

3. A method for producing a cyclic diamine represented by formula (4) or a salt thereof:

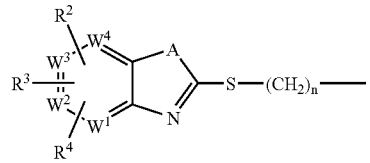

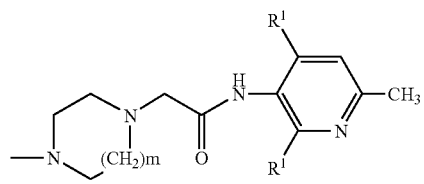

wherein A is NH, O, or S; each of $W^1$ to $W^4$ is CH, or one of $W^1$ to $W^4$ is N; $R^1$ is a lower alkylthio group; $R^2$, $R^3$, and $R^4$ may be identical to or different from one another, and are each a hydrogen atom, a halogen atom, lower alkyl group, lower alkoxy group, lower alkoxycarbonyl group, halo lower alkyl group, halo lower alkoxy group, lower alkoxy lower alkyl group, lower alkoxy lower alkoxy group, hydroxy lower alkyl group, hydroxy lower alkoxy group, lower alkylcarbonyl group, lower alkylthio group, lower alkylsulfinyl group, lower alkylsulfonyl group, nitro group, or cyano group or a salt thereof, the method comprising converting the hydroxyl group of a 2-hydroxyacetylaminopyridine compound represented by formula (1):

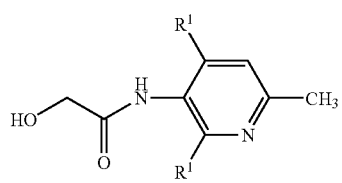

wherein $R^1$ has the same meaning as described above to a aryl or alkyl sulfonyloxy group to thereby produce an aryl or alkyl sulfonyloxyacetylaminopyridine compound represented by formula (2):

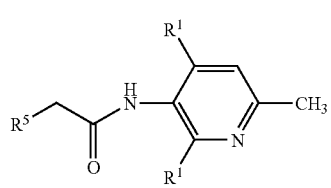

wherein $R^5$ is an aryl or alkyl group, and $R^1$ has the same meaning as described above and, subsequently reacting the aryl or alkyl sulfonyloxyacetylaminopyridine (2) with a piperazine represented by formula (3):

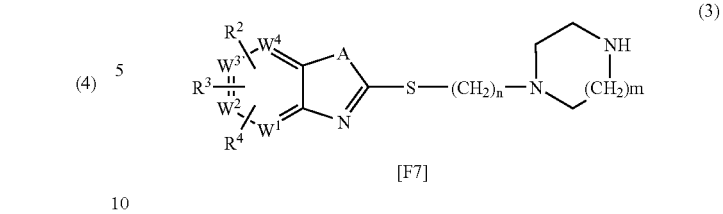

[F7]

wherein A, $W^1$ to $W^4$, $R^2$ to $R^4$, m and n have the same meanings as described above or a salt thereof.

4. A aryl or alkyl sulfonyloxyacetylaminopyridine compound represented by formula (2):

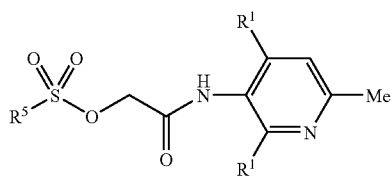

wherein $R^1$ is a lower alkylthio group, and $R^5$ is an aryl or alkyl group.

5. A method for producing a cyclic diamine represented by formula (4) or a salt thereof:

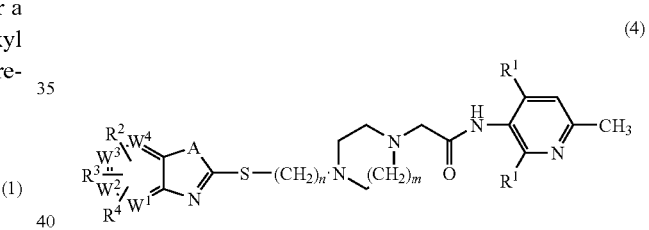

wherein A is NH, O, or S; each of $W^1$ to $W^4$ CH, or one of $W^1$ to $W^4$ is N; $R^1$ is a lower alkylthio group; $R^2$, $R^3$, and $R^4$ may be identical to or different from one another, and are each a hydrogen atom, a halogen atom, lower alkyl group, lower alkoxy group, lower alkoxycarbonyl group, halo lower alkyl group, halo lower alkoxy group, lower alkoxy lower alkyl group, lower alkoxy lower alkoxy group, hydroxy lower alkyl group, hydroxy lower alkoxy group, lower alkylcarbonyl group, lower alkylthio group, lower alkylsulfinyl group, lower alkylsulfonyl group, nitro group, or cyano group or a salt thereof, the method comprising converting the hydroxyl group of a 2-hydroxyacetylaminopyridine compound represented by formula (1):

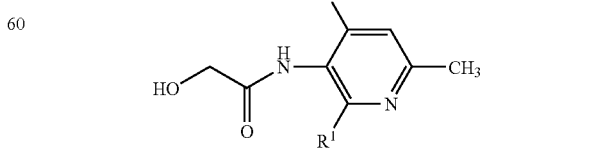

wherein $R^1$ has the same meaning as described above, to an aryl or alkyl sulfonyloxy group to thereby produce an aryl or alkyl sulfonyloxyacetylaminopyridine compound represented by formula (2):

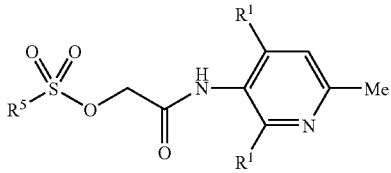

wherein $R^5$ is an aryl or alkyl group, and $R^1$ has the same meaning as described above, converting the sulfonyloxy group of the compound (2) to a halogen atom to thereby produce a haloacetylaminopyridine compound represented by formula (2'):

(2')

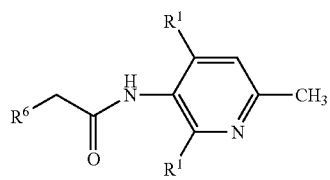

wherein $R^6$ is a halogen atom, and $R^1$ has the same meaning as described above, and, subsequently reacting the haloacetylaminopyridine (2') with a piperazine represented by formula (3):

(3)

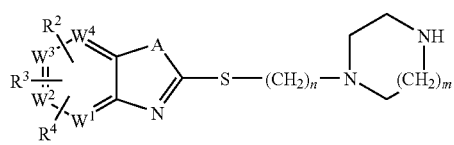

wherein A, $W^1$ to $W^4$, $R^2$ to $R^4$, m and n have the same meanings as described above or a salt thereof.

6. The method of claim 3, wherein $R^5$ is an alkyl group.

7. The method of claim 6, wherein $R^5$ is selected from the group consisting of methyl, chloromethyl, ethyl, and propyl.

8. The method of claim 3, wherein the method produces the cyclic diamine of formula (4).

9. The method of claim 3, wherein $R^5$ is an aryl group.

10. The method of claim 9, wherein $R^5$ is selected from the group consisting of

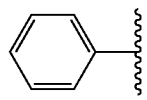

and

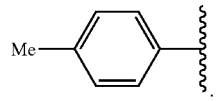

11. The compound of claim 4, wherein $R^5$ is an alkyl group.

12. The compound of claim 11, wherein $R^5$ is selected from the group consisting of methyl, chloromethyl, ethyl, and propyl.

13. The compound of claim 4, wherein $R^5$ is an aryl group.

14. The compound of claim 13, wherein $R^5$ is selected from the group consisting of

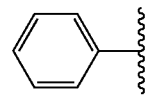

and

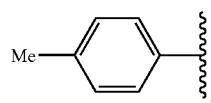

15. The method of claim 5, wherein $R^5$ is an alkyl group.

16. The method of claim 15, wherein $R^5$ is selected from the group consisting of methyl, chloromethyl, ethyl, and propyl.

17. The method of claim 5, wherein the method produces the cyclic diamine of formula (4).

18. The method of claim 5, wherein $R^5$ is an aryl group.

19. The method of claim 18, wherein $R^5$ is selected from the group consisting of

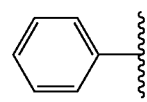

and

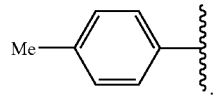

20. The method of claim 5, wherein the halogen atom $R^6$ is selected from the group consisting of chlorine, bromine and iodine.

* * * * *

UNITED STATES PATENT AND TRADEMARK OFFICE
CERTIFICATE OF CORRECTION

PATENT NO. : 7,576,203 B2  Page 1 of 1
APPLICATION NO. : 11/631397
DATED : August 18, 2009
INVENTOR(S) : Kimiyuki Shibuya et al.

It is certified that error appears in the above-identified patent and that said Letters Patent is hereby corrected as shown below:

Column 21, Claim 3, lines 51-63,

" 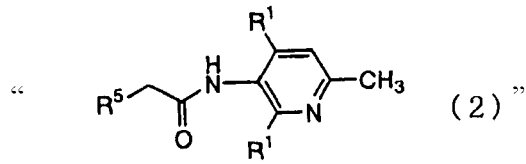 (2) "

should read:

-- 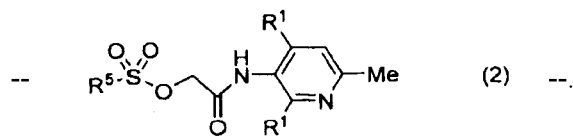 (2) --.

Column 22, Claim 5, line 43, "$W^4CH$," should read -- $W^4$ is CH --.

Signed and Sealed this

Fifteenth Day of June, 2010

David J. Kappos
*Director of the United States Patent and Trademark Office*